(12) United States Patent
Malinoski et al.

(10) Patent No.: US 9,186,674 B2
(45) Date of Patent: *Nov. 17, 2015

(54) POLYCARBONATE MICROFLUIDIC ARTICLES

(71) Applicant: SABIC Innovative Plastics IP B.V., Bergen op Zoom (NL)

(72) Inventors: Jon M. Malinoski, Zionsville, IN (US); Bret William Baumgarten, San Rafael, CA (US)

(73) Assignee: SABIC GLOBAL TECHNOLOGIES B.V. (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/163,675

(22) Filed: Jan. 24, 2014

(65) Prior Publication Data
US 2014/0206041 A1    Jul. 24, 2014

Related U.S. Application Data

(60) Provisional application No. 61/756,378, filed on Jan. 24, 2013.

(51) Int. Cl.
| | | |
|---|---|---|
| *B01L 3/00* | (2006.01) | |
| *C12Q 1/68* | (2006.01) | |
| *C08L 67/02* | (2006.01) | |
| *C08L 69/00* | (2006.01) | |

(52) U.S. Cl.
CPC ........... *B01L 3/50851* (2013.01); *B01L 3/5027* (2013.01); *B01L 3/5085* (2013.01); *C08L 67/02* (2013.01); *C08L 69/005* (2013.01); *C12Q 1/686* (2013.01); *B01L 2200/12* (2013.01); *B01L 2300/0829* (2013.01); *C08L 2666/18* (2013.01)

(58) Field of Classification Search
CPC .............. B01L 3/5085; B01L 3/50853; B01L 2300/0829; B01L 2300/0819; C12M 23/12; C12M 25/04
See application file for complete search history.

(56) References Cited

U.S. PATENT DOCUMENTS

| | | | | |
|---|---|---|---|---|
| 4,917,671 | A | 4/1990 | Chang | |
| 6,307,005 | B1 * | 10/2001 | Davis et al. | 528/196 |
| 6,340,589 | B1 | 1/2002 | Turner et al. | |
| 6,485,283 | B1 * | 11/2002 | Yamaguchi et al. | 425/72.1 |

(Continued)

FOREIGN PATENT DOCUMENTS

| | | | |
|---|---|---|---|
| EP | 433716 A2 * | 6/1991 | |
| EP | 0542422 A1 | 5/1993 | |

(Continued)

OTHER PUBLICATIONS

Copending U.S. Appl. No. 14/163,701, filed Jan. 24, 2014.

(Continued)

*Primary Examiner* — Jill Warden
*Assistant Examiner* — Matthew Krcha
(74) *Attorney, Agent, or Firm* — Cantor Colburn LLP

(57) ABSTRACT

Microfluidic devices, and methods for their use are described. The microfluidic devices include articles formed from a thermoplastic composition comprising a poly(aliphatic ester)-polycarbonate comprising soft block ester units, derived from monomers comprising an alpha, omega $C_{6-20}$ aliphatic dicarboxylic acid or derivative thereof, a dihydroxyaromatic compound, and a carbonate source.

30 Claims, 2 Drawing Sheets

(56) References Cited

U.S. PATENT DOCUMENTS

| | | |
|---|---|---|
| 6,528,302 B2 | 3/2003 | Turner et al. |
| 6,753,404 B2 * | 6/2004 | Suh et al. ............... 528/196 |
| 6,941,057 B1 | 9/2005 | Okamoto et al. |
| 7,347,977 B2 | 3/2008 | Guelzow et al. |
| 2002/0017805 A1 * | 2/2002 | Carroll et al. ............ 296/189 |
| 2003/0108449 A1 | 6/2003 | Reihs et al. |
| 2004/0018117 A1 * | 1/2004 | Desmond et al. ........... 422/64 |
| 2005/0058578 A1 * | 3/2005 | Guelzow et al. ........... 422/102 |
| 2005/0232818 A1 | 10/2005 | Sandell et al. |
| 2007/0031296 A1 * | 2/2007 | Coulling et al. ........... 422/102 |
| 2007/0135569 A1 * | 6/2007 | DeRudder ................. 525/67 |
| 2007/0243523 A1 * | 10/2007 | Ionescu-Zanetti et al. ..... 435/4 |
| 2008/0000917 A1 | 1/2008 | Agarwal et al. |
| 2008/0176289 A1 * | 7/2008 | Zeng et al. ............... 435/91.2 |
| 2009/0186966 A1 * | 7/2009 | Gallucci et al. ............ 524/96 |
| 2010/0028988 A1 | 2/2010 | Chu et al. |
| 2010/0168370 A1 | 7/2010 | Hatano et al. |
| 2010/0175999 A1 | 7/2010 | Barlow et al. |
| 2011/0071261 A1 * | 3/2011 | Hoeks et al. ............... 525/418 |
| 2011/0286897 A1 | 11/2011 | Uschkureit et al. |

FOREIGN PATENT DOCUMENTS

| | | |
|---|---|---|
| EP | 605979 * | 7/1994 |
| EP | 0999033 A2 | 5/2000 |
| EP | 1893979 B1 | 3/2008 |
| EP | 11346772 B1 | 12/2011 |
| JP | 2007285835 A | 11/2007 |
| JP | 4530895 B2 | 8/2010 |
| JP | 4706533 B2 | 6/2011 |
| WO | 0158688 A1 | 8/2001 |
| WO | 2005028109 A2 | 3/2005 |
| WO | WO2006104260 A1 | 10/2006 |

OTHER PUBLICATIONS

Copending U.S. Appl. No. 14/163,809, filed Jan. 24, 2014.

* cited by examiner

POLYCARBONATE MICROFLUIDIC ARTICLES

This application claims priority on U.S. provisional application 61/756,378 filed Jan. 24, 2013, the disclosure of which is incorporated herein by reference in its entirety.

TECHNICAL FIELD

The disclosure generally relates to a thermoplastic composition with flowability for use in thin walled articles.

BACKGROUND

Thin walled articles are commonly used in the medical field, for example in microfluidic and/or polymerase chain reaction (PCR) applications. Microfluidic applications deal with the precise control of fluids that are geometrically constrained in microfluidic devices that can be characterized in general by the presence of one or more channels with at least one dimension of less than or equal to 1 millimeter (mm). Obtaining microfluidic devices that can achieve accurate fine mold detail replication and that can allow for the production of channels with such small dimensions is a constant challenge.

Considering PCR applications, PCR is a process used to amplify and copy a piece of DNA sequence across multiple orders of magnitude and is a vital technique in the field of molecular biology. In the PCR process, the DNA fragment is mixed in aqueous solution with complementary DNA primers and DNA polymerase enzyme and the mixture is taken through several thermal cycling steps. This thermal cycling process separates the double-helix of the target DNA sequence and initiates new DNA synthesis through the DNA polymerase catalyst. A typical thermal profile for the PCR reaction is shown below in Table 1, where ° C. is degrees Celsius.

TABLE 1

| Step | Time Duration | Temperature (° C.) |
| --- | --- | --- |
| Initial Denaturation | 2 minutes | 94-95 |
| Denaturation | 20-30 seconds | 94-95 |
| Primer Extension | 1 minute | 72 |
| Final Extension | 5-15 minutes | 72 |

The PCR reactions are typically carried out in microwells in arrays from 8 to 96 wells and volumes of 0.2-0.5 milliliters (mL). Due to the high number of samples in each microwell plate, the Society of Biomolecular Screening and the American National Standards Institute (ANSI) have published standards ANSI/SBS 1-2004 through 4-2004 for microwell plates concerning the particular dimensions and positions of the microwells for microwell plates having 96, 984, and 1536 wells.

Efficient heat transfer through the walls of the microwell to the reaction solution is required for strict temperature control during the PCR reaction process. In order to achieve efficient heat transfer, the PCR trays are designed with very thin microwell wall thicknesses, such as around 0.2 mm. Injection molding of these thin-wall trays becomes a significant challenge since an extremely high flow material is required to fill the thin microwell walls. In addition, the material needs to have sufficient heat resistance to avoid deformation during the PCR thermal cycling step, and optical clarity is desired so the liquid volume level can be observed. Typically, a polypropylene such as PD702 from LYONDELL BASELL is used for injection molding of the PCR trays. However, polypropylene is subject to softening at elevated temperatures such as those used in PCR denaturation cycles, which can cause PCR or other microfluidic components to become excessively flexible during processing, and/or be subject to warping or other physical deformation, and/or leaking.

Polycarbonate materials have not typically been used for thin-wall microfluidic applications such as PCR microwells because while many polycarbonates possess the clarity and high heat resistance desired for the PCR or other microfluidic applications, they have generally been thought to lack sufficient flow to fill the thin tooling required and/or do not have sufficient ductility at room temperature. Accordingly, polypropylene has generally been the thermoplastic of choice for PCR and other microfluidic applications.

While a number of microfluidic and/or PCR devices fabricated from polypropylene or other materials that have been used for such devices have been proposed, there is a continuing need in the art for materials for use in making thin walled articles that are compatible with the microfluidic and/or PCR operating conditions.

SUMMARY

As further described herein, microfluidic devices can include articles formed from a thermoplastic composition comprising a poly(aliphatic ester)-polycarbonate comprising soft block ester units, derived from monomers comprising an alpha, omega $C_{6-20}$ aliphatic dicarboxylic acid or derivative thereof, a dihydroxyaromatic compound, and a carbonate source.

In some embodiments, the microfluidic device, comprising a poly(aliphatic ester)-polycarbonate comprising soft block ester units, derived from monomers comprising an alpha, omega $C_{6-20}$ aliphatic dicarboxylic acid or derivative thereof, a dihydroxyaromatic compound, and a carbonate source, is a PCR microwell or a PCR microwell plate.

Also, as described in further detail below, a method of using a microfluidic device for processing fluids comprises
  exposing a portion of the device to a processing temperature at least 90° C.;
  wherein the portion of the device exposed to the processing temperature includes an article formed from a thermoplastic composition comprising:
  a poly(aliphatic ester)-polycarbonate comprising soft block ester units, derived from monomers comprising an alpha, omega $C_{6-20}$ aliphatic dicarboxylic acid or derivative thereof, a dihydroxyaromatic compound, and a carbonate source.

Also provided is a microfluidic device for processing fluids at a process temperature of at least 90° C., the device comprising an article exposed to the process temperature formed from a thermoplastic composition comprising a thermoplastic composition comprising
  a poly(aliphatic ester)-polycarbonate comprising soft block ester units, derived from monomers comprising an alpha, omega $C_{6-20}$ aliphatic dicarboxylic acid or derivative thereof, a dihydroxyaromatic compound, and a carbonate source.

BRIEF DESCRIPTION OF THE DRAWINGS

For a more complete understanding of the present application, reference is now made to the following descriptions taken in conjunction with the accompanying figures in which.

DETAILED DESCRIPTION

Figure 1:
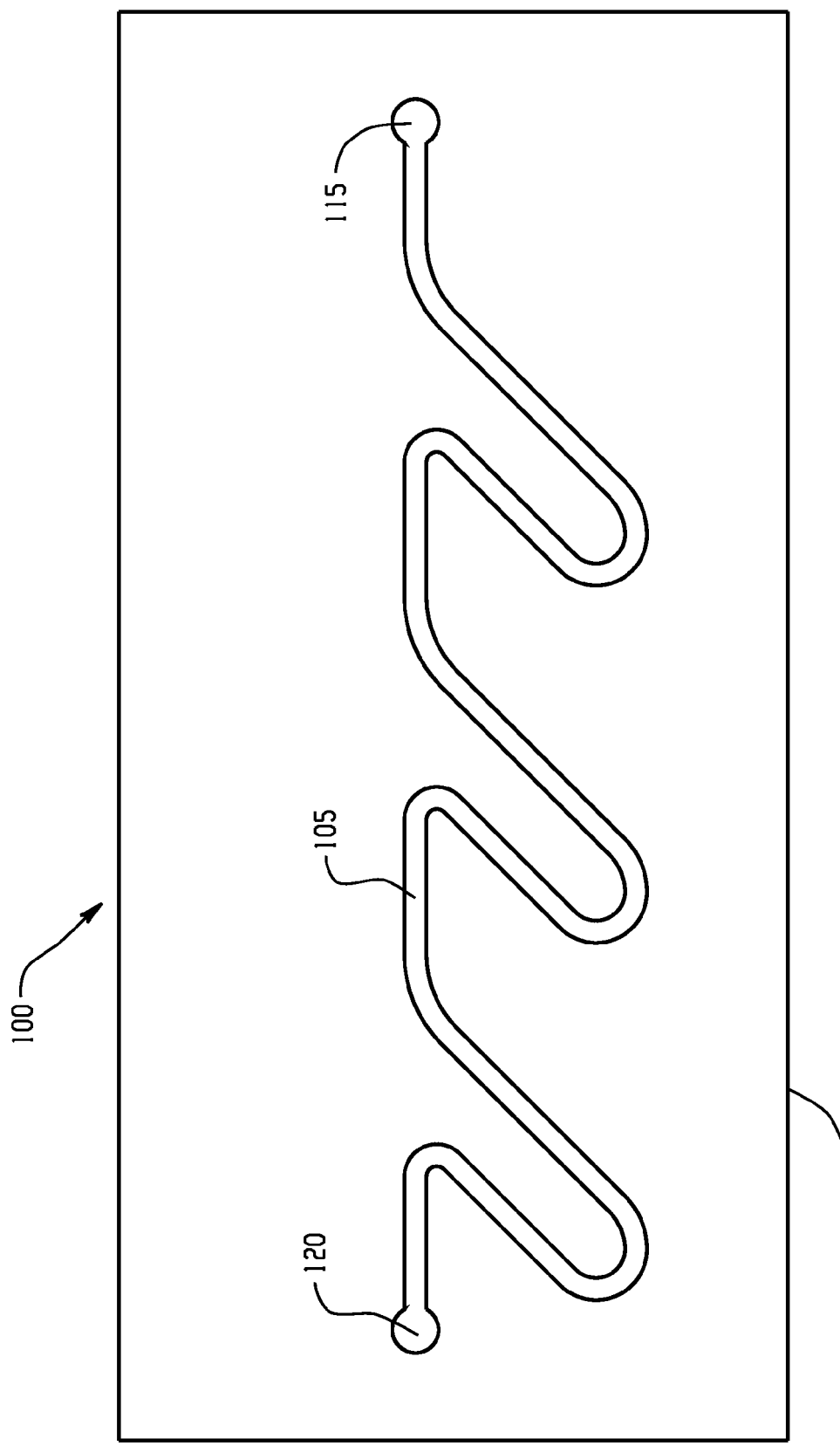
FIG. 1 is an illustration of a typical microfluidic plate.

The thermoplastic composition used to make the microfluidic devices described herein is also referred to as the high flow thermoplastic composition that comprises polycarbonate, specifically a polyester-polycarbonate copolymer, more specifically a poly(aliphatic ester)-polycarbonate copolymer. Generally, as used herein, the term "polycarbonate" refers to the repeating structural carbonate units of the formula (1)

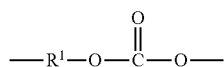
(1)

in which at least 60 percent of the total number of $R^1$ groups contain aromatic moieties and the balance thereof are aliphatic, alicyclic, or aromatic. Each $R^1$ can be an aromatic radical of the formula -$A^1$-$Y^1$-$A^2$. Each $R^1$ can comprise a $C_{6-30}$ aromatic group, that is, contains at least one aromatic moiety. $R^1$ can be derived from a dihydroxy compound of the formula HO—$R^1$—OH, in particular of formula (2)

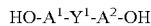
(2)

wherein each of $A^1$ and $A^2$ is a monocyclic divalent aromatic group and $Y^1$ is a single bond or a bridging group having one or more atoms that separate $A^1$ from $A^2$. In an embodiment, one atom separates $A^1$ from $A^2$. Illustrative non-limiting examples of radicals of this type are —O—, —S—, —S(O)—, S(O)$_2$—, —C(O)—, methylene, cyclohexylmethylene, 2-[2.2.1]-bicycloheptylidene, ethylidene, isopropylidene, neopentylidene, cyclohexylidene, cyclopentadecylidene, cyclododecylidene, and adamantylidene. The bridging radical $Y^1$ can be a hydrocarbon group or a saturated hydrocarbon group such as methylene, cyclohexylidene, or isopropylidene. Specifically, the $R^1$ groups can be derived from a dihydroxy aromatic compound of formula (3)

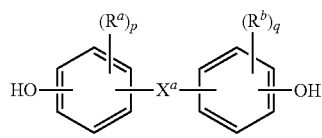
(3)

wherein $R^a$ and $R^b$ are each independently a halogen, $C_{1-12}$ alkoxy, or $C_{1-12}$ alkyl; and p and q are each independently integers of 0 to 4. It will be understood that $R^a$ is hydrogen when p is 0, and likewise $R^b$ is hydrogen when q is 0. Also in formula (3), $X^a$ is a bridging group connecting the two hydroxy-substituted aromatic groups, where the bridging group and the hydroxy substituent of each $C_6$ arylene group are disposed ortho, meta, or para (specifically para) to each other on the $C_6$ arylene group. Examples of the bridging group $X^a$ include a single bond, —O—, —S—, —S(O)—, S(O)$_2$—, —C(O)—, or a $C_{1-18}$ organic group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group. In an embodiment, p and q are each 1, and $R^a$ and $R^b$ are each a $C_{1-3}$ alkyl group, specifically methyl, disposed meta to the hydroxy group on each arylene group. $X^a$ can be a substituted or unsubstituted $C_{3-18}$ cycloalkylidene, a $C_{1-25}$ alkylidene of formula —C($R^c$)($R^d$)— wherein $R^c$ and $R^d$ are each independently hydrogen, $C_{1-12}$ alkyl, $C_{1-12}$ cycloalkyl, $C_{7-12}$ arylalkyl, $C_{1-12}$ heteroalkyl, or cyclic $C_{7-12}$ heteroarylalkyl, or a group of the formula —C(=$R^e$)— wherein $R^e$ is a divalent $C_{1-12}$ hydrocarbon group such as methylene, cyclohexylmethylene, ethylidene, neopentylidene, and isopropylidene, as well as 2-[2.2.1]-bicycloheptylidene, cyclohexylidene, cyclopentylidene, cyclododecylidene, or adamantylidene.

Bisphenols containing substituted or unsubstituted cyclohexane units can also be used as a dihydroxy compound, for example bisphenols of the formula (4)

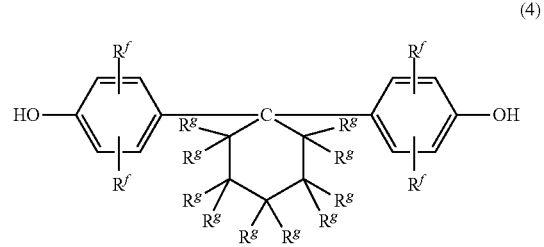
(4)

wherein each $R^f$ is independently hydrogen, $C_{1-12}$ alkyl, or halogen; and each $R^g$ is independently hydrogen or $C_{1-12}$ alkyl. The substituents can be aliphatic or aromatic, straight chain, cyclic, bicyclic, branched, saturated, or unsaturated. Such cyclohexane-containing bisphenols, for example the reaction product of two moles of a phenol with one mole of a hydrogenated isophorone, can be used to make polycarbonate polymers with high glass transition temperatures and high heat distortion temperatures. Cyclohexyl bisphenol containing polycarbonates, or a combination comprising at least one of the foregoing with other bisphenol polycarbonates, are supplied by BAYER CO. under the APEC* trade name.

Other aromatic dihydroxy compounds of the formula HO—$R^1$—OH include compounds of formula (5)

(5)

wherein each $R^h$ is independently a halogen atom, a $C_{1-10}$ hydrocarbyl such as a $C_{1-10}$ alkyl group, a halogen-substituted $C_{1-10}$ alkyl group, a $C_{6-10}$ aryl group, or a halogen-substituted $C_{6-10}$ aryl group, and n is 0 to 4. The halogen can be bromine.

Some illustrative examples of specific aromatic dihydroxy compounds include the following: 4,4'-dihydroxybiphenyl, 1,6-dihydroxynaphthalene, 2,6-dihydroxynaphthalene, bis (4-hydroxyphenyl)methane, bis(4-hydroxyphenyl)diphenylmethane, bis(4-hydroxyphenyl)-1-naphthylmethane, 1,2-bis (4-hydroxyphenyl)ethane, 1,1-bis(4-hydroxyphenyl)-1-phenylethane, 2-(4-hydroxyphenyl)-2-(3-hydroxyphenyl) propane, bis(4-hydroxyphenyl)phenylmethane, 2,2-bis(4-hydroxy-3-bromophenyl)propane, 1,1-bis(hydroxyphenyl) cyclopentane, 1,1-bis(4-hydroxyphenyl)cyclohexane, 1,1-bis(4-hydroxyphenyl)isobutene, 1,1-bis(4-hydroxyphenyl) cyclododecane, trans-2,3-bis(4-hydroxyphenyl)-2-butene, 2,2-bis(4-hydroxyphenyl)adamantane, alpha, alpha'-bis(4-hydroxyphenyl)toluene, bis(4-hydroxyphenyl)acetonitrile, 2,2-bis(3-methyl-4-hydroxyphenyl)propane, 2,2-bis(3-ethyl-4-hydroxyphenyl)propane, 2,2-bis(3-n-propyl-4-hydroxyphenyl)propane, 2,2-bis(3-isopropyl-4-hydroxyphenyl)propane, 2,2-bis(3-sec-butyl-4-hydroxyphenyl)propane, 2,2-bis(3-t-butyl-4-hydroxyphenyl)propane, 2,2-bis(3-cyclohexyl-4-hydroxyphenyl)propane, 2,2-bis(3-allyl-4-hydroxyphenyl)propane, 2,2-bis(3-methoxy-4-hydroxyphenyl)propane, 2,2-bis(4-hydroxyphenyl)hexafluoropropane, 1,1-dichloro-2,2-bis(4-hydroxyphenyl)ethylene, 1,1-dibromo-2,2-bis(4-hydroxyphenyl)ethylene, 1,1-dichloro-2,2-bis(5-phenoxy-4-hydroxyphenyl)ethylene, 4,4'-dihydroxybenzophenone, 3,3-bis(4-hydroxyphenyl)-2-butanone, 1,6-bis(4-hydroxyphenyl)-1,6-hexanedione, ethylene glycol bis(4-hydroxyphenyl)ether, bis(4-hydroxyphenyl)ether, bis(4-hydroxyphenyl)sulfide, bis(4-hydroxyphenyl)sulfoxide, bis(4-hydroxyphenyl)sulfone, 9,9-bis(4-hydroxyphenyl)fluorine, 2,7-dihydroxypyrene, 6,6'-dihydroxy-3,3,3',3'-tetramethylspiro(bis)indane ("spirobiindane bisphenol"), 3,3-bis(4-hydroxyphenyl)phthalimide, 2,6-dihydroxydibenzo-p-dioxin, 2,6-dihydroxythianthrene, 2,7-dihydroxyphenoxathin, 2,7-dihydroxy-9,10-dimethylphenazine, 3,6-dihydroxydibenzofuran, 3,6-dihydroxydibenzothiophene, and 2,7-dihydroxycarbazole, resorcinol, substituted resorcinol compounds such as 5-methyl resorcinol, 5-ethyl resorcinol, 5-propyl resorcinol, 5-butyl resorcinol, 5-t-butyl resorcinol, 5-phenyl resorcinol, 5-cumyl resorcinol, 2,4,5,6-tetrafluoro resorcinol, 2,4,5,6-tetrabromo resorcinol, or the like; catechol; hydroquinone; substituted hydroquinones such as 2-methyl hydroquinone, 2-ethyl hydroquinone, 2-propyl hydroquinone, 2-butyl hydroquinone, 2-t-butyl hydroquinone, 2-phenyl hydroquinone, 2-cumyl hydroquinone, 2,3,5,6-tetramethyl hydroquinone, 2,3,5,6-tetra-t-butyl hydroquinone, 2,3,5,6-tetrafluoro hydroquinone, 2,3,5,6-tetrabromo hydroquinone, or the like, or combinations comprising at least one of the foregoing dihydroxy compounds.

Specific examples of bisphenol compounds of formula (3) include 1,1-bis(4-hydroxyphenyl)methane, 1,1-bis(4-hydroxyphenyl)ethane, 2,2-bis(4-hydroxyphenyl)propane (hereinafter "bisphenol A" or "BPA"), 2,2-bis(4-hydroxyphenyl)butane, 2,2-bis(4-hydroxyphenyl)octane, 1,1-bis(4-hydroxyphenyl)propane, 1,1-bis(4-hydroxyphenyl)n-butane, 2,2-bis(4-hydroxy-2-methylphenyl)propane, 1,1-bis(4-hydroxy-t-butylphenyl)propane, 3,3-bis(4-hydroxyphenyl)phthalimidine, 2-phenyl-3,3-bis(4-hydroxyphenyl) phthalimidine (PPPBP), and 1,1-bis(4-hydroxy-3-methylphenyl)cyclohexane (DMBPC). Combinations comprising at least one of the foregoing dihydroxy compounds can also be used.

In some embodiments, the polycarbonate is a linear homopolymer derived from bisphenol A, in which each of $A^1$ and $A^2$ is p-phenylene and $Y^1$ is isopropylidene in formula (3).

The polycarbonates can have an intrinsic viscosity, as determined in chloroform at 25° C., of 0.3 to 1.5 deciliters per gram (dl/g), specifically 0.45 to 1.0 dl/g. The polycarbonates can have a weight average molecular weight ($M_w$) of 10,000 to 100,000 grams per mole (g/mol), as measured by gel permeation chromatography (GPC) using a cross-linked styrene-divinyl benzene column, at a sample concentration of 1 milligram per milliliter, and as calibrated with polycarbonate standards. The polycarbonate can have a melt volume flow rate (often abbreviated MVR) that measures the rate of extrusion of a thermoplastics through an orifice at a prescribed temperature and load. Polycarbonates for the formation of articles can have an MVR, measured at 300° C. under a load of 1.2 kg according to ASTM D1238-10 or ISO 1133, of 0.5 to 80 cubic centimeters per 10 minutes (cc/10 min).

"Polycarbonates" and "polycarbonate resins" as used herein further include homopolycarbonates, copolymers comprising different $R^1$ moieties in the carbonate (referred to herein as "copolycarbonates"), copolymers comprising carbonate units and other types of polymer units, such as ester units, polysiloxane units, and combinations comprising at least one of homopolycarbonates and copolycarbonates. As used herein, "combination" is inclusive of blends, mixtures, alloys, reaction products, and the like. A specific type of copolymer is a polyester carbonate, also known as a polyester-polycarbonate. Such copolymers further contain, in addition to recurring carbonate chain units of the formula (1), units of formula (6)

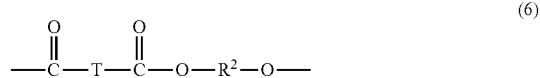

(6)

wherein $R^2$ is a divalent group derived from a dihydroxy compound, and can be, for example, a $C_{2-10}$ alkylene group, a $C_{6-20}$ alicyclic group, a $C_{6-20}$ aromatic group or a polyoxyalkylene group in which the alkylene groups contain 2 to 6 carbon atoms, specifically 2, 3, or 4 carbon atoms. $R^2$ can be a $C_{2-30}$ alkylene group having a straight chain, branched chain, or cyclic (including polycyclic) structure. Alternatively, $R^2$ can be derived from an aromatic dihydroxy compound of formula (3) above, or from an aromatic dihydroxy compound of formula (5) above. T is a divalent group derived from a dicarboxylic acid (aliphatic, aromatic, or alkyl aromatic), and can be, for example, a $C_{4-18}$ aliphatic group, a $C_{6-20}$ alkylene group, a $C_{6-20}$ alicyclic group, a $C_{6-20}$ alkyl aromatic group, or a $C_{6-20}$ aromatic group.

Examples of aromatic dicarboxylic acids that can be used to prepare the polyester units include isophthalic or terephthalic acid, 1,2-di(p-carboxyphenyl)ethane, 4,4'-dicarboxydiphenyl ether, 4,4'-bisbenzoic acid, and combinations comprising at least one of the foregoing acids. Acids containing fused rings can also be present, such as in 1,4-, 1,5-, or 2,6-naphthalenedicarboxylic acids. Specific dicarboxylic acids are terephthalic acid, isophthalic acid, naphthalene dicarboxylic acid, cyclohexane dicarboxylic acid, or combinations thereof. A specific dicarboxylic acid comprises a combination of isophthalic acid and terephthalic acid wherein the weight ratio of isophthalic acid to terephthalic acid is 91:9 to 2:98. In another specific embodiment, $R^2$ is a $C_{2-6}$ alkylene group and T is p-phenylene, m-phenylene, naphthalene, a divalent cycloaliphatic group, or a combination thereof. This class of polyester includes the poly(alkylene terephthalates).

The molar ratio of ester units to carbonate units in the copolymers can vary broadly, for example 1:99 to 99:1, specifically 10:90 to 90:10, more specifically 25:75 to 75:25, depending on the desired properties of the final composition.

The thermoplastic composition can comprise a polyester-polycarbonate copolymer, specifically a polyester-polycarbonate copolymer in which the ester units of formula (6) comprise soft block ester units, also referred to herein as aliphatic dicarboxylic acid ester units. Such a polyester-polycarbonate copolymer comprising soft block ester units is also referred to herein as a poly(aliphatic ester)-polycarbonate. The soft block ester unit can be a $C_{6-20}$ aliphatic dicarboxylic acid ester unit (where $C_{6-20}$ includes the terminal carboxyl groups), and can be straight chain (i.e., unbranched) or branched chain dicarboxylic acids, cycloalkyl or cycloalkylidene-containing dicarboxylic acids units, or combinations of these structural units. In some embodiments, the $C_{6-20}$ aliphatic dicarboxylic acid ester unit includes a straight chain alkylene group comprising methylene ($—CH_2—$) repeating units. In some embodiments, a soft block ester unit comprises units of formula (6a)

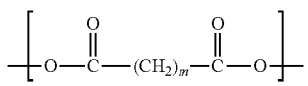

wherein m is 4 to 18, more specifically 8 to 10. The poly(aliphatic ester)-polycarbonate can include less than or equal to 25 weight % of the soft block unit. The poly(aliphatic ester)-polycarbonate can comprise units of formula (6a) in an amount of 0.5 to 10 weight %, specifically 2 to 9 weight %, and more specifically 3 to 8 weight %, based on the total weight of the poly(aliphatic ester)-polycarbonate. The poly(aliphatic ester)-polycarbonate can have a glass transition temperature of 110 to 145° C., specifically 115 to 145° C., more specifically 128 to 139° C., even more specifically 130 to 139° C.

The poly(aliphatic ester)-polycarbonate is a copolymer of soft block ester units with carbonate units. The poly(aliphatic ester)-polycarbonate is shown in formula (6b)

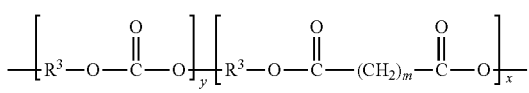

where each $R^3$ is independently derived from a dihydroxyaromatic compound of formula (3) or (5), m is 4 to 18, and x and y each represent average weight percentages of the poly(aliphatic ester)-polycarbonate where the average weight percentage ratio x:y is 10:90 to 0.5:99.5, specifically 9:91 to 1:99, and more specifically 8:92 to 3:97, where x+y is 100.

Soft block ester units, as defined herein, can be derived from an alpha, omega $C_{6-20}$, specifically, $C_{10-12}$, aliphatic dicarboxylic acid or a reactive derivative thereof. The carboxylate portion of the aliphatic ester unit of formula (6a), in which the terminal carboxylate groups are connected by a chain of repeating methylene (—$CH_2$—) units (where m is as defined for formula (6a)), can be derived from the corresponding dicarboxylic acid or reactive derivative thereof, such as the acid halide (specifically, the acid chloride), an ester, or the like. Exemplary alpha, omega dicarboxylic acids (from which the corresponding acid chlorides can be derived) include alpha, omega $C_6$ dicarboxylic acids such as hexanedioic acid (also referred to as adipic acid); alpha, omega $C_{10}$ dicarboxylic acids such as decanedioic acid (also referred to as sebacic acid); and alpha, omega $C_{12}$ dicarboxylic acids such as dodecanedioic acid (sometimes abbreviated as DDDA). It will be appreciated that the aliphatic dicarboxylic acid is not limited to these exemplary carbon chain lengths, and that other chain lengths within the $C_{6-20}$ limitation can be used. In some embodiments, the poly(aliphatic ester)-polycarbonate having soft block ester units comprising a straight chain methylene group and a bisphenol A polycarbonate group is shown in formula (6c)

where m is 4 to 18 and x and y are as defined for formula (6b). In an embodiment, the poly(aliphatic ester)-polycarbonate copolymer comprises sebacic acid ester units and bisphenol A carbonate units (formula (6c), where m is 8, and the average weight ratio of x:y is 6:94).

The poly(aliphatic ester)-polycarbonate copolymer, as described above, can be a polycarbonate having aliphatic dicarboxylic acid ester soft block units randomly incorporated along the copolymer chain. The introduction of the soft block segment (e.g., a flexible chain of repeating $CH_2$ units) in the polymer chain of a polycarbonate reduces the glass transition temperatures ($T_g$) of the resulting soft block containing polycarbonate copolymer. These materials are generally transparent and have higher melt volume ratios than polycarbonate homopolymers or copolymers without the soft block.

The poly(aliphatic ester)-polycarbonate copolymer, i.e., a polycarbonate having aliphatic dicarboxylic acid ester soft block units randomly incorporated along the copolymer chain, has soft block segment (e.g., a flexible chain of repeating —$CH_2$— units) in the polymer chain, where inclusion of these soft block segments in a polycarbonate reduces the glass transition temperatures ($T_g$) of the resulting soft block-containing polycarbonate copolymer. These thermoplastic compositions, comprising soft block in amounts of 0.5 to 10 wt % of the weight of the poly(aliphatic ester)-polycarbonate, are transparent and have higher MVR than polycarbonate homopolymers or copolymers without the soft block.

The poly(aliphatic ester)-polycarbonate can have clarity and light transmission properties, where a sufficient amount of light with which to make photometric or fluorometric measurement of specimens contained within the channels and/or wells of an article made thereof can pass through the thermoplastic composition. The poly(aliphatic ester)-polycarbonate can have 80 to 100% transmission, more specifically, 89 to 100% light transmission as determined by ASTM D1003-11, using 3.2 mm thick plaques. The poly(aliphatic ester)-polycarbonate can also have low haze, specifically 0.001 to 5%, more specifically, 0.001 to 1% as determined by ASTM D1003-11 using 3.2 mm thick plaques.

While the soft block units of the poly(aliphatic ester)-polycarbonate copolymers cannot be specifically limited to the alpha, omega $C_{6-20}$ dicarboxylic acids disclosed herein, it is believed that shorter soft block chain lengths (less than $C_6$, including the carboxylic acid groups) cannot provide sufficient chain flexibility in the poly(aliphatic ester)polycarbonate to increase the MVR to the desired levels (i.e., greater than or equal to 13 cc/10 min at 250° C. and 1.2 kg load); likewise, increasing the soft block chain lengths (greater than $C_{20}$, including the carboxylic acid groups) can result in creation of crystalline domains within the poly(aliphatic ester)-polycarbonate composition, which in turn can lead to phase separation of the domains that can manifest as reduced transparency and increased haze, and can affect the thermal properties such as $T_g$ (where multiple $T_g$ values can result for different phase separated domains) and MVR (decreasing MVR to values of less than 13 cc/10 min at 250° C. and 1.2 kg load).

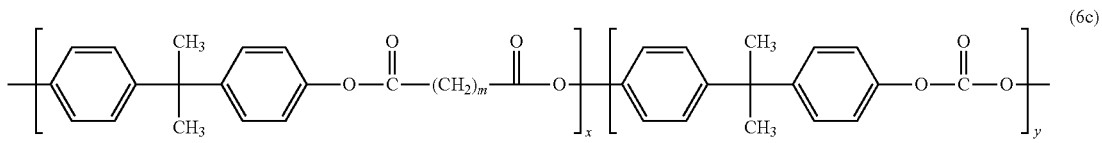

Exemplary thermoplastic compositions include poly(sebacic acid ester)-co-(bisphenol A carbonate). It will be understood that a wide variety of thermoplastic compositions and articles derived from them can be obtained by not only changing the thermoplastic compositions (e.g., by replacing sebacic acid with adipic acid in the poly(sebacic acid ester)-co-(bisphenol A carbonate) but by changing the amounts of sebacic or other aliphatic acid content in the blends while maintaining a constant molecular weight or while varying the molecular weight. Similarly, new thermoplastic compositions can be identified by changing the molecular weights of the components in the exemplary copolymer blends while keeping, for example, sebacic acid content constant.

The ductility, transparency and melt flow of the thermoplastic compositions may be varied by the composition of the poly(aliphatic ester)-polycarbonate. For example, wt % of aliphatic dicarboxylic acid ester units (e.g., sebacic acid) may be varied from 1 to 10 wt % of the total weight of the thermoplastic composition. The distribution (in the polymer chain) of the sebacic acid (or other dicarboxylic acid ester) in the copolymers may also be varied by choice of synthetic method of the poly(aliphatic ester)-polycarbonate copolymers (e.g., interfacial, melt processed, or further reactive extrusion of a low MVR poly(aliphatic ester)-polycarbonate with a redistribution catalyst) to obtain the desired properties. In this way, thermoplastic compositions having high flow (e.g. MVR of up to 25 cc/10 min. at 1.2 Kg and 250° C.) may further be achieved where the poly(aliphatic ester)-polycarbonate is too low in MVR, or is opaque (where the soft blocks are too great in length, the concentration of the soft block in the copolymer is too high, or where the overall molecular weight of the copolymer is too high, or where the copolymer has a block architecture in which the soft block units in the copolymer aggregate to form larger blocks), while transparent products with greater than or equal to 85% transmission, haze of less than 1% (measured on a 3.2 mm thick molded plaque), and high flow (e.g., up to an MVR of 25 cc/10 min. at 1.2 Kg and 250° C.), and ductility may be obtained. Thermoplastic compositions having this combination of properties is not obtainable from polycarbonate compositions of, for example, bisphenol A polycarbonate homopolymer absent a poly(aliphatic ester)-polycarbonate copolymer.

Polyester-polycarbonate copolymers generally can have a weight average molecular weight ($M_w$) of 1,500 to 100,000 grams per mole (g/mol), specifically 1,700 to 50,000 g/mol. In an embodiment, poly(aliphatic ester)-polycarbonates have a molecular weight of 15,000 to 45,000 g/mol, specifically 17,000 to 40,000 g/mol, more specifically 20,000 to 30,000 g/mol, and still more specifically 20,000 to 25,000 g/mol. Molecular weight determinations are performed using gel permeation chromatography (GPC), using a cross-linked styrene-divinylbenzene column and calibrated to polycarbonate references. Samples are prepared at a concentration of 1 milligram (mg)/mL, and are eluted at a flow rate of 1.0 mL/min.

Polyester-polycarbonates can exhibit melt flow rates as described by the melt volume ratio (MVR) of 5 to 150 cubic centimeters (cc)/10 min, specifically 7 to 125 cc/10 min, more specifically 9 to 110 cc/10 min, and still more specifically 10 to 100 cc/10 min, measured at 300° C. and a load of 1.2 kg according to ASTM D1238-10. The poly(aliphatic ester)-polycarbonate can have an MVR of 66 to 150 g/10 min, and more specifically 100 to 150 g/10 min, measured at 300° C. and under a load of 1.2 kilograms according to ASTM D1238-10. Commercial polyester blends with polycarbonate are marketed under the trade name XYLEX®, including for example XYLEX® X7300, and commercial polyester-polycarbonates are marketed under the trade name LEXAN® SLX polymers, including for example LEXAN® SLX-9000, and are available from SABIC Innovative Plastics (formerly GE Plastics). In an embodiment, poly(aliphatic ester)-polycarbonates have an MVR of 13 to 25 cc/10 min, and more specifically 15 to 22 cc/10 min, measured at 250° C. and under a load of 1.2 kilograms and a dwell time of 6 minutes, according to ASTM D1238-10. Also in an embodiment, poly (aliphatic ester)-polycarbonates have an MVR of 13 to 25 cc/10 min, and more specifically 15 to 22 cc/10 min, measured at 250° C. and under a load of 1.2 kilograms and a dwell time of 4 minutes, according to ISO 1133.

The thermoplastic composition can further comprise another thermoplastic polymer such as a polycarbonate polyester copolymer different from the poly(aliphatic ester)-polycarbonate copolymer, a polycarbonate, a polyester, a polysiloxane-polycarbonate copolymer, or combinations comprising one or more of the foregoing.

The thermoplastic composition can thus comprise poly (aliphatic ester)-polycarbonate copolymer, and optionally a polycarbonate polymer not identical to the poly(aliphatic ester)-polycarbonate. Such added polycarbonate polymer may be included but is not essential to the thermoplastic composition. In an embodiment, where desired, the thermoplastic composition may include the polycarbonate in amounts of less than or equal to 50 wt %, based on the total weight of poly(aliphatic ester)-polycarbonate and any added polycarbonate. Specifically useful in the thermoplastic polymer include homopolycarbonates, copolycarbonates, polyester-polycarbonates, polysiloxane-polycarbonates, blends thereof with polyesters, and combinations comprising at least one of the foregoing polycarbonate-type resins or blends. It should further be noted that the inclusion of other polymers such as polycarbonate is permitted provided the desired properties of the thermoplastic composition are not significantly adversely affected. In a specific embodiment, a thermoplastic composition consists essentially of a poly(aliphatic ester)-polycarbonate copolymer. In another specific embodiment, the thermoplastic composition consists of poly(aliphatic ester)-polycarbonate copolymer.

When the poly(aliphatic ester)-polycarbonate is blended with other polymer, the thermoplastic composition can comprise polycarbonate, including blends of polycarbonate homo and/or copolymers, polyesters, polyester-polycarbonates other than the poly(aliphatic ester)-polycarbonates disclosed above, or polysiloxane-polycarbonate in an amount of less than or equal to 50 wt %, specifically 1 to 50 wt %, and more specifically 10 to 50 wt %, based on the total weight of poly(aliphatic ester)-polycarbonate and any added polycarbonate, provided the addition of the polycarbonate does not significantly adversely affect the desired properties of the thermoplastic composition. Where a polycarbonate is used in addition to the poly(aliphatic ester)-polycarbonate, the polycarbonate (or a combination of polycarbonates, i.e., a polycarbonate composition) can have an MVR measured at 300° C. under a load of 1.2 kg according to ASTM D1238-10 or ISO 1133, of 45 to 75 cc/10 min, specifically 50 to 70 cc/10 min, and more specifically 55 to 65 cc/10 min.

Polyesters can include, for example, polyesters having repeating units of formula (6), which include poly(alkylene dicarboxylates), liquid crystalline polyesters, and polyester copolymers. The polyesters described herein are generally completely miscible with the polycarbonates when blended.

Such polyesters generally include aromatic polyesters, poly(alkylene esters) including poly(alkylene arylates), and poly(cycloalkylene diesters). Aromatic polyesters can have a polyester structure according to formula (8), wherein D and T are each aromatic groups as described hereinabove. In an embodiment, aromatic polyesters can include, for example, poly(isophthalate-terephthalate-resorcinol) esters, poly(isophthalate-terephthalate-bisphenol A) esters, poly[(isophthalate-terephthalate-resorcinol) ester-co-(isophthalate-terephthalate-bisphenol A)]ester, or a combination comprising at least one of these. Also contemplated are aromatic polyesters with a minor amount, e.g., 0.5 to 10 wt %, based on the total weight of the polyester, of units derived from an aliphatic diacid and/or an aliphatic polyol to make copolyesters. Poly(alkylene arylates) can have a polyester structure according to formula (8), wherein T comprises groups derived from aromatic dicarboxylates, cycloaliphatic dicarboxylic acids, or derivatives thereof. Examples of specific T groups include 1,2-, 1,3-, and 1,4-phenylene; 1,4- and 1,5-naphthylenes; cis- or trans-1,4-cyclohexylene; and the like. Specifically, where T is 1,4-phenylene, the poly(alkylene arylate) is a poly(alkylene terephthalate). In addition, for poly(alkylene arylate), specific alkylene groups D include, for example, ethylene, 1,4-butylene, and bis-(alkylene-disubstituted cyclohexane) including cis- and/or trans-1,4-(cyclohexylene)dimethylene. Examples of poly(alkylene terephthalates) include poly(ethylene terephthalate) (PET), poly(1,4-butylene terephthalate) (PBT), and poly(propylene terephthalate) (PPT). Poly(alkylene naphthoates), such as poly(ethylene naphthanoate) (PEN), and poly(butylene naphthanoate) (PBN), or poly(cycloalkylene diesters) such as poly(cyclohexanedimethylene terephthalate) (PCT), can also be used. Combinations comprising at least one of the foregoing polyesters can also be used.

Copolymers comprising alkylene terephthalate repeating ester units with other ester groups can also be used. Ester units can include different alkylene terephthalate units, which can be present in the polymer chain as individual units, or as blocks of poly(alkylene terephthalates). Specific examples of such copolymers include poly(cyclohexanedimethylene terephthalate)-co-poly(ethylene terephthalate), abbreviated as PETG where the polymer comprises greater than or equal to 50 mole % of poly(ethylene terephthalate), and abbreviated as PCTG where the polymer comprises greater than 50 mole % of poly(1,4-cyclohexanedimethylene terephthalate).

Poly(cycloalkylene diester)s can also include poly(alkylene cyclohexanedicarboxylate)s. Of these, a specific example is poly(1,4-cyclohexane-dimethano 1-1,4-cyclohexanedicarboxylate) (PCCD), having recurring units of formula (7)

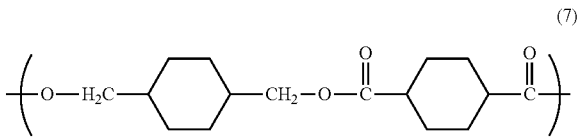

(7)

wherein, as described using formula (6), $R^2$ is a 1,4-cyclohexanedimethylene group derived from 1,4-cyclohexanedimethanol, and T is a cyclohexane ring derived from cyclohexanedicarboxylate or a chemical equivalent thereof, and can comprise the cis-isomer, the trans-isomer, or a combination comprising at least one of the foregoing isomers.

The polyesters can be obtained by interfacial polymerization or melt-process condensation as described above, by solution phase condensation, or by transesterification polymerization wherein, for example, a dialkyl ester such as dimethyl terephthalate can be transesterified with ethylene glycol using acid catalysis, to generate poly(ethylene terephthalate). It is possible to use a branched polyester in which a branching agent, for example, a glycol having three or more hydroxyl groups or a trifunctional or multifunctional carboxylic acid has been incorporated. Furthermore, it is sometimes desirable to have various concentrations of acid and hydroxyl end groups on the polyester, depending on the ultimate end use of the composition.

The thermoplastic composition can comprise a polysiloxane-polycarbonate copolymer, also referred to as a polysiloxane-polycarbonate. The polysiloxane (also referred to herein as "polydiorganosiloxane") blocks of the copolymer comprise repeating siloxane units (also referred to herein as "diorganosiloxane units") of formula (8):

(8)

wherein each occurrence of R is same or different, and is a $C_{1-13}$ monovalent organic radical. For example, R can independently be a $C_{1-13}$ alkyl group, $C_{1-13}$ alkoxy group, $C_{2-13}$ alkenyl group, $C_{2-13}$ alkenyloxy group, $C_{3-6}$ cycloalkyl group, $C_{3-6}$ cycloalkoxy group, $C_{6-14}$ aryl group, $C_{6-10}$ aryloxy group, $C_{7-13}$ arylalkyl group, $C_{7-13}$ arylalkoxy group, $C_{7-13}$ alkylaryl group, or $C_{7-13}$ alkylaryloxy group. The foregoing groups can be fully or partially halogenated with fluorine, chlorine, bromine, or iodine, or a combination thereof. Combinations of the foregoing R groups can be used in the same copolymer.

The value of D in formula (8) can vary widely depending on the type and relative amount of each component in the thermoplastic composition, the desired properties of the composition, and like considerations. Generally, D can have an average value of 2 to 1,000, specifically 2 to 500, more specifically 5 to 100. In an embodiment, D has an average value of 30 to 60, specifically 40 to 60. In another embodiment, D has an average value of 45.

Where D is of a lower value, e.g., less than 40, it can be desirable to use a relatively larger amount of the polycarbonate-polysiloxane copolymer. Conversely, where D is of a higher value, e.g., greater than 40, it can be necessary to use a relatively lower amount of the polycarbonate-polysiloxane copolymer.

A combination of a first and a second (or more) polysiloxane-polycarbonate copolymer can be used, wherein the average value of D of the first copolymer is less than the average value of D of the second copolymer. In one embodiment, the polydiorganosiloxane blocks are provided by repeating structural units of formula (9):

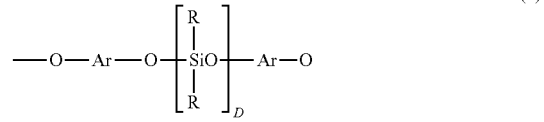

(9)

wherein D is as defined above; each R can independently be the same or different, and is as defined above; and each Ar can independently be the same or different, and is a substituted or unsubstituted $C_{6-30}$ arylene radical, wherein the bonds are directly connected to an aromatic moiety. Ar groups in formula (9) can be derived from a $C_{6-30}$ dihydroxyarylene compound, for example a dihydroxyarylene compound of formula (2), (3), or (5) above. Combinations comprising at least one of the foregoing dihydroxyarylene compounds can also be used. Specific examples of dihydroxyarylene compounds are 1,1-bis(4-hydroxyphenyl)methane, 1,1-bis(4-hydroxyphenyl)ethane, 2,2-bis(4-hydroxyphenyl)propane, 2,2-bis(4-hydroxyphenyl)butane, 2,2-bis(4-hydroxyphenyl)octane, 1,1-bis(4-hydroxyphenyl)propane, 1,1-bis(4-hydroxyphenyl)n-butane, 2,2-bis(4-hydroxy-1-methylphenyl)propane, 1,1-bis(4-hydroxyphenyl)cyclohexane, bis(4-hydroxyphenylsulphide), and 1,1-bis(4-hydroxy-t-butylphenyl)propane. Combinations comprising at least one of the foregoing dihydroxy compounds can also be used.

Units of formula (9) can be derived from the corresponding dihydroxy compound of formula (10)

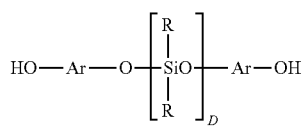

(10)

wherein R, Ar, and D are as described above. Compounds of formula (10) can be obtained by the reaction of a dihydroxyarylene compound with, for example, an alpha, omega-bisacetoxypolydiorgano siloxane under phase transfer conditions.

In another embodiment, polydiorganosiloxane blocks comprise units of formula (11)

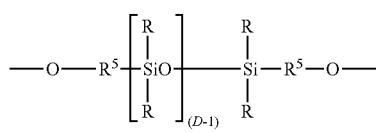

(11)

wherein R and D are as described above, and each occurrence of R is independently a divalent $C_{1-30}$ alkylene, and wherein the polymerized polysiloxane unit is the reaction residue of its corresponding dihydroxy compound. In a specific embodiment, the polydiorganosiloxane blocks are provided by repeating structural units of formula (12)

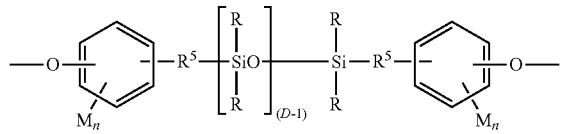

(12)

wherein R and D are as defined above. Each $R^5$ in formula (12) is independently a divalent $C_{2-8}$ aliphatic group. Each M in formula (12) can be the same or different, and can be a halogen, cyano, nitro, $C_{1-8}$ alkylthio, $C_{1-8}$ alkyl, $C_{2-8}$ alkoxy, $C_{2-8}$ alkenyl, $C_{3-8}$ alkenyloxy group, $C_{3-8}$ cycloalkyl, $C_{3-8}$ cycloalkoxy, $C_{6-10}$ aryl, $C_{6-10}$ aryloxy, $C_{7-12}$ arylalkyl, $C_{7-12}$ arylalkoxy, $C_{7-12}$ alkylaryl, or $C_{7-12}$ alkylaryloxy, wherein each n is independently 0, 1, 2, 3, or 4.

In some embodiments, M is bromo or chloro, an alkyl group such as methyl, ethyl, or propyl, an alkoxy group such as methoxy, ethoxy, or propoxy, or an aryl group such as phenyl, chlorophenyl, or tolyl; $R^5$ is a dimethylene, trimethylene or tetramethylene group; and R is a $C_{1-8}$ alkyl, haloalkyl such as trifluoropropyl, cyanoalkyl, or aryl such as phenyl, chlorophenyl or tolyl. In some embodiments, R is methyl, or a mixture of methyl and trifluoropropyl, or a mixture of methyl and phenyl. In still another embodiment, M is methoxy, n is one, $R^5$ is a divalent $C_{1-3}$ aliphatic group, and R is methyl.

Units of formula (12) can be derived from the corresponding dihydroxy polydiorganosiloxane (13)

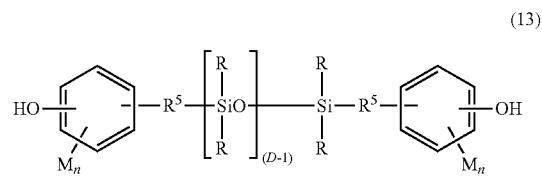

(13)

wherein R, D, M, $R^5$, and n are as described above. Such dihydroxy polysiloxanes can be made by effecting a platinum catalyzed addition between a siloxane hydride of formula (14)

(14)

wherein R and D are as previously defined, and an aliphatically unsaturated monohydric phenol. Aliphatically unsaturated monohydric phenols include, for example, eugenol, 2-allylphenol, 4-allyl-2-methylphenol, 4-allyl-2-phenylphenol, 4-allyl-2-bromophenol, 4-allyl-2-t-butoxyphenol, 4-phenyl-2-phenylphenol, 2-methyl-4-propylphenol, 2-allyl-4,6-dimethylphenol, 2-allyl-4-bromo-6-methylphenol, 2-allyl-6-methoxy-4-methylphenol and 2-allyl-4,6-dimethylphenol. Mixtures comprising at least one of the foregoing can also be used.

Polysiloxane-polycarbonates comprise 50 to 99.9 wt % of carbonate units and 0.1 to 50 wt % siloxane units, based on the total weight of the polysiloxane-polycarbonate. Specific polysiloxane-polycarbonate copolymers comprise 90 to 99 wt %, specifically 75 to 99 wt %, of carbonate units and 1 to 25 wt %, specifically 1 to 10 wt %, siloxane units. An exemplary polysiloxane-polycarbonate copolymer can comprise 6 wt % siloxane units. Another exemplary polysiloxane-polycarbonate comprises 20 wt % siloxane units. All references to weight percent compositions in the polysiloxane-polycarbonate are based on the total weight of the polysiloxane-polycarbonate Exemplary polysiloxane-polycarbonates comprise polysiloxane units derived from dimethylsiloxane units (e.g., formula (11) where R is methyl), and carbonate units derived from bisphenol A, e.g., the dihydroxy compound of formula (3) in which each of $A^1$ and $A^2$ is p-phenylene and $Y^1$ is isopropylidene. Polysiloxane-polycarbonates can have a weight average molecular weight of 2,000 to 100,000 g/mol, specifically 5,000 to 50,000 g/mol. Some specific polysiloxane-polycarbonates have, for example, a weigh average molecular weight of 15,000 to 45,000 g/mol. Molecular weights referred to herein are as measured by gel permeation chromatography using a cross-linked styrene-divinyl benzene column, at a sample concentration of 1 milligram per milliliter, and as calibrated with polycarbonate standards.

A polysiloxane-polycarbonate can have a melt volume flow rate, measured at 300° C. under a load of 1.2 kg, of 1 to 50 cc/10 min, specifically 2 to 30 cc/10 min. In an embodiment, the polysiloxane-polycarbonate has a melt volume rate measured at 300° C. under a load of 1.2 kg, of 5 to 15 cc/10 min, specifically 6 to 14 cc/10 min, and specifically 8 to 12 cc/10 min mixtures of polysiloxane-polycarbonates of different flow properties can be used to achieve the overall desired flow property. In an embodiment, exemplary polysiloxane-polycarbonates are marketed under the trade name LEXAN® EXL polycarbonates, available from SABIC Innovative Plastics (formerly GE Plastics).

The thermoplastic composition can further include various other additives ordinarily incorporated with thermoplastic compositions of this type, where the additives are selected so as not to significantly adversely affect the desired properties of the thermoplastic composition. Mixtures of additives can be used. Such additives can be mixed at a suitable time during the mixing of the components for forming the thermoplastic composition.

Additives contemplated herein include, but are not limited to, impact modifiers, fillers, colorants including dyes and pigments, antioxidants, heat stabilizers, light and/or UV light stabilizers, reinforcing agents, light reflecting agents, surface effect additives, plasticizers, lubricants, mold release agents, flame retardants, antistatic agents, anti-drip agents, radiation (gamma) stabilizers, and the like, or a combination comprising at least one of the foregoing additives. A combination of additives can be used, for example a combination of a heat stabilizer, mold release agent, and ultraviolet light stabilizer. Specifically, a combination of additives can be used comprising one or more of an antioxidant such as IRGAPHOS*, pentaerythritol stearate, a compatibilizer such as JONCRYL* epoxy, a quaternary ammonium compound such as tetramethyl ammonium hydroxide or tetrabutyl ammonium hydroxide, and a quaternary phosphonium compound such as tetrabutyl phosphonium hydroxide or tetrabutyl phosphonium acetate. In general, the additives are used in the amounts generally known to be effective. The total amount of additives (other than any impact modifier, filler, or reinforcing agents) is generally 0.01 to 5 weight %, based on the total weight of the composition. While it is contemplated that other resins and/or additives can be used in the thermoplastic compositions described herein, such additives while desirable in some exemplary embodiments are not essential.

The thermoplastic composition can comprise poly(aliphatic ester)-polycarbonate in an amount of 50 to 100 wt %, based on the total weight of poly(aliphatic ester)-polycarbonate and any added polycarbonate. The thermoplastic composition can comprise only poly(aliphatic ester)-polycarbonate. The thermoplastic composition can comprise poly(aliphatic ester)-polycarbonate that has been reactively extruded to form a reaction product. The thermoplastic composition can comprise a blend of poly(aliphatic ester)-polycarbonate that has been reactively extruded.

The thermoplastic composition can comprise a soft block content (i.e., an alpha, omega $C_{6-20}$ dicarboxylic acid ester unit content) of 0.5 to 10 wt %, specifically 1 to 9 wt %, and more specifically 3 to 8 wt %, based on the total weight of the poly(aliphatic ester)-polycarbonate copolymer and any added polycarbonate.

The thermoplastic composition can have clarity and light transmission properties, where a sufficient amount of light with which to make photometric or fluorometric measurement of specimens contained within the channels and/or wells of an article made thereof can pass through the thermoplastic composition. Thermoplastic composition can have 80 to 100% transmission, more specifically, 89 to 100% light transmission as determined by ASTM D1003-11, using 3.2 mm thick plaques. The thermoplastic composition can also have low haze, specifically 0.001 to 5%, more specifically, 0.001 to 1% as determined by ASTM D1003-11 using 3.2 mm thick plaques.

The thermoplastic composition can have an MVR of greater than or equal to 13 cc/10 min, specifically of 13 to 25 cc/10 min at 300° C. under a load of 1.2 kg), more specifically of 15 to 22 cc/10 min at 300° C. under a load of 1.2 kg according to ASTM D1238-10.

The thermoplastic compositions can further have an HDT of greater than or equal to 100° C., more specifically of 100 to 140° C. measured at 1.82 mega Pascal (MPa) using unannealed 3.2 mm plaques according to ASTM D648-07. The thermoplastic compositions can also have an HDT of greater than or equal to 115° C., more specifically of 115 to 155° C. measured at 0.45 MPa using unannealed 3.2 mm plaques according to ASTM D648-07.

The thermoplastic compositions can further have a Notched Izod Impact of 400 to 700 Joules per meter (J/m) or 510 to 650 J/m, measured at 23° C. using ⅛-inch thick bars (3.18 mm) in accordance with ASTM D256-10. The thermoplastic compositions can further have a Notched Izod Impact ductilities of 30 to 100% or 50 to 100%, measured at 23° C. using ⅛-inch thick bars (3.18 mm) in accordance with ASTM D256-10.

The thermoplastic compositions can have an instrumented impact energy at peak of 40 to 80 J/m or 50 to 70 J/m, measured at 23° C. in accordance with ASTM D3763-10. The thermoplastic compositions can have an instrumented impact ductility of 65 to 100% or 85 to 100% measured at 23° C. in accordance with ASTM D3763-10.

The thermoplastic compositions can have a tensile or a flexural modulus of 1500 to 3500 MPa or 2000 to 3000 MPa measured at 0.2 inches (in)/min (approximately 5.0 mm/min) in accordance with ASTM D638-10. The thermoplastic compositions can have a tensile stress at yield of 35 to 100 MPa or 50 to 80 MPa measured at 0.2 in/min in accordance with ASTM D638-10. The thermoplastic compositions can have a tensile stress at break of 35 to 100 MPa or 50 to 80 MPa measured at 0.2 in/min in accordance with ASTM D638-10. The polycarbonate compositions can have a tensile strain at yield of 2 to 10% or 5 to 8% measured at 0.2 in/min in accordance with ASTM D638-10. The thermoplastic compositions can have a tensile strain at break of 85 to 150% or 95 to 110% measured at 0.2 in/min in accordance with ASTM D638-10.

Polycarbonates and polyestercarbonates can be manufactured by processes such as interfacial polymerization and melt polymerization. Although the reaction conditions for interfacial polymerization can vary, an exemplary process generally involves dissolving or dispersing a dihydric phenol reactant in aqueous caustic soda or potash, adding the resulting mixture to a water-immiscible solvent medium, and contacting the reactants with a carbonate precursor in the presence of a catalyst such as, for example, a tertiary amine or a phase transfer catalyst, under controlled pH conditions, e.g., 8 to 10. The most commonly used water immiscible solvents include methylene chloride, 1,2-dichloroethane, chlorobenzene, toluene, and the like.

Exemplary carbonate precursors include, for example, a carbonyl halide such as carbonyl bromide or carbonyl chloride, or a haloformate such as a bishaloformates of a dihydric phenol (e.g., the bischloroformates of bisphenol A, hydroquinone, or the like) or a glycol (e.g., the bishaloformate of ethylene glycol, neopentyl glycol, polyethylene glycol, or the like). Combinations comprising at least one of the foregoing types of carbonate precursors can also be used. In an exemplary embodiment, an interfacial polymerization reaction to form carbonate linkages uses phosgene as a carbonate precursor, and is referred to as a phosgenation reaction.

Among tertiary amines that can be used are aliphatic tertiary amines such as triethylamine, tributylamine, cycloaliphatic amines such as N,N-diethyl-cyclohexylamine and aromatic tertiary amines such as N,N-dimethylaniline.

Among the phase transfer catalysts that can be used are catalysts of the formula $(R^3)_4Q^+X$, wherein each $R^3$ is the same or different, and is a $C_{1-10}$ alkyl group; Q is a nitrogen or phosphorus atom; and X is a halogen atom or a $C_{1-8}$ alkoxy group or $C_{6-18}$ aryloxy group. Exemplary phase transfer catalysts include, for example, $[CH_3(CH_2)_3]_4NX$, $[CH_3(CH_2)_3]_4PX$, $[CH_3(CH_2)_5]_4NX$, $[CH_3(CH_2)_6]_4NX$, $[CH_3(CH_2)_4]_4NX$, $CH_3[CH_3(CH_2)_3]_3NX$, and $CH_3[CH_3(CH_2)_2]_3NX$, wherein X is Cl$^-$, Br$^-$, a $C_{1-8}$ alkoxy group or a $C_{6-18}$ aryloxy group. An effective amount of a phase transfer catalyst can be 0.1 to 10 weight percent (wt %) based on the weight of bisphenol in the phosgenation mixture. In another embodiment, an effective amount of phase transfer catalyst can be 0.5 to 2 wt % based on the weight of bisphenol in the phosgenation mixture.

When an interfacial polymerization is used as the polymerization method, rather than utilizing the dicarboxylic acid (such as the alpha, omega $C_{6-20}$ aliphatic dicarboxylic acid) per se, it is possible to employ the reactive derivatives of the dicarboxylic acid, such as the corresponding dicarboxylic acid halides, and in particular the acid dichlorides and the acid dibromides. Thus, for example instead of using isophthalic acid, terephthalic acid, or a combination comprising at least one of the foregoing (for poly(arylate ester)-polycarbonates), it is possible to employ isophthaloyl dichloride, terephthaloyl dichloride, and a combination comprising at least one of the foregoing. Similarly, for the poly(aliphatic ester)-polycarbonates, it is possible to use, for example, acid chloride derivatives such as a $C_6$ dicarboxylic acid chloride (adipoyl chloride), a $C_{10}$ dicarboxylic acid chloride (sebacoyl chloride), or a $C_{12}$ dicarboxylic acid chloride (dodecanedioyl chloride). The dicarboxylic acid or reactive derivative can be condensed with the dihydroxyaromatic compound in a first condensation, followed by in situ phosgenation to generate the carbonate linkages with the dihydroxyaromatic compound. Alternatively, the dicarboxylic acid or derivative can be condensed with the dihydroxyaromatic compound simultaneously with phosgenation.

Alternatively, melt processes can be used to make the polycarbonates. Generally, in the melt polymerization process, polycarbonates can be prepared by co-reacting, in a molten state, the dihydroxy reactant(s) and a diaryl carbonate ester, such as diphenyl carbonate, in the presence of a transesterification catalyst in a BANBURY* mixer, twin screw extruder, or the like to form a uniform dispersion. Volatile monohydric phenol is removed from the molten reactants by distillation and the polymer is isolated as a molten residue. A specific melt process for making polycarbonates uses a diaryl carbonate ester having electron-withdrawing substituents on the aryls. Examples of specific diaryl carbonate esters with electron withdrawing substituents include bis(4-nitrophenyl)carbonate, bis(2-chlorophenyl)carbonate, bis(4-chlorophenyl)carbonate, bis(methyl salicyl)carbonate, bis(4-methylcarboxylphenyl)carbonate, bis(2-acetylphenyl)carboxylate, bis(4-acetylphenyl)carboxylate, or a combination comprising at least one of the foregoing. In addition, transesterification catalysts for use can include phase transfer catalysts of formula $(R^4)_4QA$ above, wherein each $R^4$, Q, and X are as defined above. Examples of transesterification catalysts include tetrabutylammonium hydroxide, methyltributylammonium hydroxide, tetrabutylammonium acetate, tetrabutylphosphonium hydroxide, tetrabutylphosphonium acetate, tetrabutylphosphonium phenolate, or a combination comprising at least one of the foregoing.

All types of polycarbonate end groups are contemplated in the polycarbonate composition, provided that such end groups do not significantly adversely affect desired properties of the compositions.

Branched polycarbonate blocks can be prepared by adding a branching agent during polymerization. These branching agents include polyfunctional organic compounds containing at least three functional groups selected from hydroxyl, carboxyl, carboxylic anhydride, haloformyl, and mixtures of the foregoing functional groups. Specific examples include trimellitic acid, trimellitic anhydride, trimellitic trichloride, tris-p-hydroxy phenyl ethane, isatin-bisphenol, tris-phenol TC (1,3,5-tris((p-hydroxyphenyl)isopropyl)benzene), tris-phenol PA (4(4(1,1-bis(p-hydroxyphenyl)-ethyl)alpha, alpha-dimethyl benzyl)phenol), 4-chloroformyl phthalic anhydride, trimesic acid, and benzophenone tetracarboxylic acid. The branching agents can be added at a level of 0.05 to 2.0 weight %. Mixtures comprising linear polycarbonates and branched polycarbonates can be used.

A chain stopper (also referred to as a capping agent) can be included during polymerization. The chain stopper limits molecular weight growth rate, and so controls molecular weight in the polycarbonate. Exemplary chain stoppers include certain mono-phenolic compounds, mono-carboxylic acid chlorides, and/or mono-chloroformates. Mono-phenolic chain stoppers are exemplified by monocyclic phenols such as phenol and $C_{1-22}$ alkyl-substituted phenols such as p-cumyl-phenol, resorcinol monobenzoate, and p- and tertiary-butyl phenol; and monoethers of diphenols, such as p-methoxyphenol. Alkyl-substituted phenols with branched chain alkyl substituents having 8 to 9 carbon atom can be specifically mentioned. Certain mono-phenolic UV absorbers can also be used as a capping agent, for example 4-substituted-2-hydroxybenzophenones and their derivatives, aryl salicylates, monoesters of diphenols such as resorcinol monobenzoate, 2-(2-hydroxyaryl)-benzotriazoles and their derivatives, 2-(2-hydroxyaryl)-1,3,5-triazines and their derivatives, and the like.

Mono-carboxylic acid chlorides can also be used as chain stoppers. These include monocyclic, mono-carboxylic acid chlorides such as benzoyl chloride, $C_{1-22}$ alkyl-substituted benzoyl chloride, toluoyl chloride, halogen-substituted benzoyl chloride, bromobenzoyl chloride, cinnamoyl chloride, 4-nadimidobenzoyl chloride, and combinations thereof; polycyclic, mono-carboxylic acid chlorides such as trimellitic anhydride chloride, and naphthoyl chloride; and combinations of monocyclic and polycyclic mono-carboxylic acid chlorides. Chlorides of aliphatic monocarboxylic acids with less than or equal to 22 carbon atoms are useful. Functionalized chlorides of aliphatic monocarboxylic acids, such as acryloyl chloride and methacryoyl chloride, are also useful. Also useful are monochloroformates including monocyclic, mono-chloroformates, such as phenyl chloroformate, alkyl-substituted phenyl chloroformate, p-cumyl phenyl chloroformate, toluene chloroformate, and combinations thereof.

Where the melt volume rate of an otherwise compositionally suitable poly(aliphatic ester)-polycarbonate is not suitably high, i.e., where the MVR is less than 13 cc/10 min when measured at 250° C., under a load of 1.2 kg, the poly(aliphatic ester)-polycarbonate can be modified to provide a reaction product with a higher flow (i.e., greater than or equal to 13 cc/10 min when measured at 250° C., under a load of 1.2 kg), by treatment using a redistribution catalyst under conditions of reactive extrusion. During reactive extrusion, the redistribution catalyst can be typically included in small amounts of less than or equal to 400 parts per million (ppm) by weight, by injecting a dilute aqueous solution of the redistribution catalyst into the extruder being fed with the poly(aliphatic ester)-polycarbonate.

The redistribution catalyst can be tetraalkylphosphonium hydroxide, tetraalkylphosphonium alkoxide, tetraalkylphosphonium aryloxide, a tetraalkylphosphonium carbonate, a tetraalkylammonium hydroxide, a tetraalkylammonium carbonate, a tetraalkylammonium phosphite, a tetraalkylammonium acetate, or a combination comprising at least one of the foregoing catalysts, wherein each alkyl is independently a $C_{1-6}$ alkyl. In a specific embodiment, a redistribution catalyst is a tetra $C_{1-6}$ alkylphosphonium hydroxide, $C_{1-6}$ alkyl phosphonium phenoxide, or a combination comprising one or more of the foregoing catalysts. An exemplary redistribution catalyst is tetra-n-butylphosphonium hydroxide.

The redistribution catalyst can be present in an amount of 40 to 120 ppm, specifically 40 to 110 ppm, and more specifically 40 to 100 ppm, by weight based on the weight of the poly(aliphatic ester)-polycarbonate.

The thermoplastic compositions described herein can be molded into shaped articles by for example injection molding (such as one-shot or two-shot injection molding), extrusion, rotational molding, blow molding, and thermoforming. Desirably, the thermoplastic composition has excellent mold filling capability due to its high flow properties.

The thermoplastic composition can be manufactured, for example, by mixing powdered poly(aliphatic ester)-polycarbonate copolymer, along with an added polycarbonate and/or additives in a HENSCHEL MIXER* high speed mixer. Other low shear processes including but not limited to hand mixing can also accomplish this blending. The blend can then be fed into the throat of an extruder via a hopper. Alternatively, one or more of the components can be incorporated into the composition by feeding directly into the extruder at the throat and/or downstream through a sidestuffer. Additives can also be compounded into a masterbatch with a desired polymeric resin and fed into the extruder. The extruder is generally operated at a temperature higher than that necessary to cause the composition to flow, but at which temperature components of the thermoplastic composition do not decompose so as to significantly adversely affect the composition. The extrudate is immediately quenched in a water bath and pelletized. The pellets, so prepared when cutting the extrudate, can be one-fourth inch long or less as desired. Such pellets can be used for subsequent molding, shaping, or forming.

In a specific embodiment, the compounding extruder is a twin-screw extruder. The extruder is typically operated at a temperature of 180 to 385° C., specifically 200 to 330° C., more specifically 220 to 300° C., wherein the die temperature can be different. The extruded thermoplastic composition is quenched in water and pelletized.

The thermoplastic compositions can be molded into shaped articles by a variety of means such as injection molding (such as one-shot or two-shot injection molding), extrusion, rotational molding, blow molding, and thermoforming with or without the application of a vacuum. In some embodiments, the molding can be done by injection molding. Desirably, the thermoplastic composition has excellent mold filling capability due to its high flow properties.

Products (e.g., articles) made from the thermoplastic composition(s) can be used in a variety of applications including thin walled articles, where transparency and ductility retention at low temperatures are both required or where transparency, precision as defined by a high degree of reproducibility, retention of mechanical properties including impact strength, and precise optical properties are required. Such a blend to provide a thermoplastic composition would reduce the residual stress in the molded article due to the improved ductility and the better flow. Shaped, formed, or molded articles comprising the thermoplastic compositions are also provided.

The high melt flow thermoplastic composition polycarbonate comprises a polyester-polycarbonate copolymer and more specifically a poly(aliphatic ester)-polycarbonate copolymer. The high melt flow thermoplastic described herein can therefore be used to make an article for use in, for example, microfluidic applications such as PCR applications, etc., wherein the article is exposed at some point during processing to temperatures of at least 90° C., more specifically at least 95° C., and even more specifically at least 98° C. In some embodiments, the processing temperature is less than or equal to 120° C., more specifically less than or equal to 110° C., even more specifically less than or equal to 105° C., and even more specifically less than or equal to 100° C. These upper and lower limits are independently combinable to form processing temperature ranges, such as an exemplary processing temperature range of 95° C. to 105° C., or an exemplary processing temperature range of 95° C. to 100° C. during functional usage. Furthermore, the high melt flow thermoplastic composition can display one or more of optical clarity, improved modulus, improved room temperature ductility, and heat resistance.

The microfluidic device can be used to handle nano and picoliter fluid volumes. Exemplary microfluidic devices described herein can be devices that are capable of handling a small amount of fluid such as less than or equal to 1000 microliters, specifically 10 picoliters to 1000 microliters, more specifically 50 picoliters to 500 microliters, even more specifically 100 picoliters to 200 microliters. In the case of microwells such as PCR microwells, exemplary microwell volume capacities can range from 1 microliter to 1000 microliters, more specifically 10 microliters to 500 microliters, and more specifically 20 microliters to 250 microliters.

The microfluidic device can be a device for use in applications where precise control and manipulation of fluids that are geometrically constrained to a small scale is desired. For example the microfluidic device can comprise a fabricated dimension of less than or equal to 1 mm, specifically from 0.005 to 1 mm, more specifically from 0.01 to 0.5 mm, even more specifically from 0.05 to 0.25 mm.

The microfluidic device can be used in the field of molecular biology for enzymatic analysis (such as glucose and lactate assays), DNA analysis (such as for PCR applications and high-throughput screening), and proteomics.

The microfluidic device can be a microfluidic plate and can be used, for example, in lab-on-chip applications, where one or more of the following processing steps is integrated onto a single chip: a pre-treatment step, a preparation step, a mixing step, a treatment step, a separation step, a reaction step, etc. The microfluidic plate can be used in continuous flow applications where fluid continuously flows through at least one channel. The channel can be a microfabricated channel and the flow can be achieved by internal forces (such as capillary forces) or by external forces (such as a pressure source or a mechanical pump). The channel can have a fabricated dimension as described above, wherein the dimension is at least one of a width or a depth of the channel, or a thickness of a wall that forms a boundary of the channel. The fabricated dimension can be a dimension of less than or equal to 1 mm, specifically from 0.005 to 1 mm more specifically from 0.01 to 0.5 mm, even more specifically from 0.05 to 0.25 mm. The channel can be fabricated by, for example, injection molding, lithographic techniques, etching, or micromachining. A top view of an exemplary microfluidic device 100 is depicted in FIG. 1, where a channel 105 is formed as described above in or on a support 110. In operation, a process fluid enters the channel 105 at channel inlet 115 and flows through the channel to channel outlet 120.

The microfluidic device can be a PCR device for use in PCR applications (such as amplitubes, caps, and microwell plates). The PCR device can be used to contain small amounts of fluid as described above and/or can comprise a fabricated dimension of less than or equal to 1 mm, specifically from 0.005 to 1 mm more specifically from 0.01 to 0.5 mm, even more specifically from 0.05 to 0.25 mm, wherein the dimension is a wall thickness and the fabrication step can be a molding step.

Figure 2:
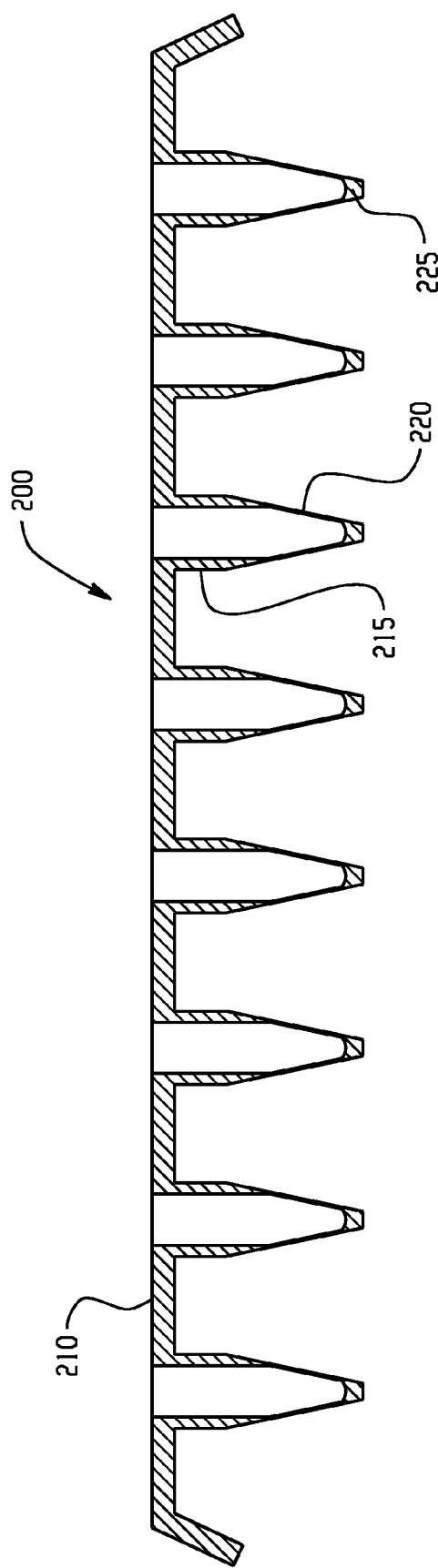
FIG. 2 is an illustration of a typical microwell plate.

The thermoplastic composition can be used in PCR devices such as PCR microwells, or in other applications requiring retention of process materials in microwells. PCR or other microwell devices can include microwells integrated into a microwell plate, as well as individual microwells, or rows or racks of microwells that can be disposed into openings of plates or other retention devices. The microwells can have various shapes including pot-shaped, shell-shaped, cup shaped, cone-shaped, tube-shaped, and the like. The microwells can be cylindrical, spherical, rectangular, hexangular, conical, and the like. The microwells can also have different shapes in different sections of the microwell plate. The microwells can have any suitable configuration including hexagonal or spherical. An exemplary embodiment of a PCR microwell plate is illustrated in cross-section view in FIG. 2, where microwell plate 200 has a plate portion 210 having a number of microwells attached through openings in plate portion 210. Each microwell comprises thick wall portion 215, thin wall portion 220, and cup-shaped bottom portion 225. The details of the attachment of the microwells to the plate portion are not shown in FIG. 2, but a number of attachment modalities are known in the art, as described further in the exemplary disclosure below. The thin wall portion 220 can have a thickness of 0.01 to 0.5 mm, more specifically from 0.05 to 0.25 mm.

The microwell plate can be designed such that the microwells do not project beyond the underside or the top side of the plate or such that they project from the underside and/or top side of the plate. Microwell plates having microwells that project from the underside of the plate are particularly suited for use in thermocyclers for PCR, since the heat exchange can take place directly between the plate of the thermocycler and the walls of the wells. When the wells project from the underside of the plate, the wells can be 3 to 30 mm in diameter and 2 to 15 mm in depth. When the wells project beyond the top side of the plate, a sealing attachment of a cover film can directly fit to the upper edges of the wells. When the wells do not project from the top side of the plate, the plate has a flat surface such that a cover plate can be laid on top of the wells to seal them. The cover plate can be made of any material such as a glass or a thermoplastic and can have adhesive properties such as pressure sensitive adhesive properties.

The plate and the microwells can be one piece or can be joined together to form one piece. The plate and microwells can be joined together by injection molding. Alternatively, the plate can have a plurality of holes, and the wells can be joined to the plate in one piece by molding onto the edges of the holes. The plate and microwells can both comprise the high melt flow thermoplastic composition or the microwells can comprise the high melt flow thermoplastic composition and the plate can be made of a different material.

The microwell plate can further be a laminate structure wherein one or more layers comprise the high melt flow thermoplastic composition. The laminate structure can be formed via coextrusion. A laminate structure can be useful in embodiments where a gas-barrier layer, a liquid-barrier layer, or the like is desired or to control the surface properties, for example hydrophobicity. A laminate structure can also be useful when reagents, such as those used in PCR techniques, can absorb certain polymers from the substrate contact with, which potentially reduces the amount of polymer absorbed and improve reaction yield.

Further description can be found in U.S. patent application Ser. No. 61/756,385 filed on Jan. 24, 2013, entitled "Microwell Plate", the disclosure of which is incorporated herein by reference in its entirety, and in U.S. patent application Ser. No. 61/756,384 filed on Jan. 24, 2013, entitled "Microwell Plate", the disclosure of which is incorporated herein by reference in its entirety.

The following examples are provided to illustrate exemplary embodiments. The examples are merely illustrative and are not intended to limit devices made in accordance with the disclosure to the materials, conditions, or process parameters set forth therein.

EXAMPLES

Molecular weight determinations were performed using GPC, using a cross-linked styrene-divinylbenzene column and calibrated to polycarbonate references. Samples are prepared at a concentration of 1 mg/mL, and are eluted at a flow rate of 1.0 mL/min.

MVR was determined at 300° C. or 250° C. using a 1.2-kilogram weight, in accordance with ASTM 1238-10.

Izod Notched Impact Strength is used to compare the impact resistances of plastic materials. Izod Impact was determined using a 3.2 mm thick, molded Izod notched impact bar per ASTM D 256-10.

Heat Deflection Temperature (HDT) is also used to compare heat resistance of plastic materials. Results were determined using a 3.2 mm thick, molded bar per ASTM D648.

Tensile properties such as Tensile Strength and Tensile Elongation to break were determined according to ASTM D 638-10.

Instrumented impact ductility was determined according to ASTM D3763-10 at 23° C.

Specific gravity was determined according to ASTM D792-08.

Light transmission and % haze were determined according to ASTM D1003-11 using 3.2 mm plaques.

Example 1 and Comparative Examples 2 and 3

Example 1 was prepared from a high melt flow thermoplastic composition that is 6.0 mole (mol) % sebacic acid and 94.0 mol % bisphenol-A with a molecular weight of 17,000 g/mol and a glass transition temperature of 135° C. Comparative Examples 2 and 3 comprise standard polycarbonate materials, PC-65 and PC-100, respectively, where PC-65 is a linear BPA polycarbonate with a molecular weight of 17,000 g/mol and PC-100 is a linear BPA polycarbonate with a molecular weight of 15,000 g/mol. The compositions of Example 1 and Comparative Examples 2 and 3 were prepared using a 30 mm co-rotating twin screw (Werner & Pfleiderer; ZSK-30) extruder using a melt temperature of 300° C. with a rate of 20 kg/hour (hr), 20 inches of mercury vacuum, and a screw speed of 400 RPM. In the case of Example 1 the IRGAPHOS solution was fed into the extruder using a separate liquid pump feeder. The extrudate was cooled under water, pelletized and dried at 120° C. for 4 hours with a desiccant bed dryer. To make test specimens, the dried pellets were injection molded using a Van Dorn 80T molding machine at 300° C. melt temperature to form test parts for impact and mechanical testing. The physical and mechanical properties of Example 1 and Comparative Examples 2 and 3 are shown in Table 2, where pph is parts per hundred resin.

duce microfluidic articles, including microwells, with wall thicknesses of 0.20 mm, whereas the lesser melt flow rates at 300 and 250° C. of 65 and 11 g/10 min, respectively, of the polycarbonate of Comparative Example 2 does not allow for the composition to have sufficient flow to fill a 0.20 mm thickness PCR tray tool.

Example 1 and Comparative Example 4

The polycarbonate composition used to make Example 1 was compared to a typical polypropylene used in commercial microwell production, PD702 from LYONDELL BASELL (Comparative Example 4) as shown in Table 3.

TABLE 2

|  |  | Example 1 | Comparative Example 2 | Comparative Example 3 |
|---|---|---|---|---|
| Material |  |  |  |  |
| HFD Low $M_w$ Copolymer |  | 100 | 0 | 0 |
| Polycarbonate 17,000 $M_w$ (PC-65) |  | 0 | 100 | 0 |
| Polycarbonate 15,000 $M_w$ (PC-100) |  | 0 | 0 | 100 |
|  |  | pph | pph | pph |
| IRGAPHOS 168 |  | 0.06 | 0.06 | 0.06 |
| PETS |  | 0.20 | 0.20 | 0.20 |
| JONCRYL ADR4368CS epoxy |  | 0.10 | 0.10 | 0.10 |
| Tetrabutyl phosphonium hydroxide, 40% solution in water |  | 0.029 | 0 | 0 |
| Mechanical |  |  |  |  |
| Tensile Modulus, 0.2 in/min | MPa | 2340 | 2390 | ** |
| Tensile Stress, yield, Type 1, 0.2 in/min | MPa | 53 | 59 | ** |
| Tensile Stress, break, Type 1, 0.2 in/min | MPa | 52 | 52 | ** |
| Tensile Strain, yield, Type 1, 0.2 in/min | % | 5.5 | 5.5 | ** |
| Tensile Strain, break, Type 1, 0.2 in/min | % | 101 | 83 | ** |
| Impact |  |  |  |  |
| Izod impact, notched 23° C. | J/m | 596 | 500 | ** |
| Izod impact, notched 23° C., % ductile | % | 100 | 20 | ** |
| Instrumented impact Energy @ peak, 23° C. | J | 62 | 34 | ** |
| Instrumented impact, 23° C., % ductile | % | 100 | 60 | ** |
| Physical |  |  |  |  |
| Specific Gravity | — | 1.20 | 1.20 | 1.20 |
| Melt Flow Rate, 300° C. | cm³/10 min | 94 | 61 | 94 |
| Melt Flow Rate, 250° C. | cm³/10 min | 17.9 | 10.4 | 17.9 |
| Thermal |  |  |  |  |
| HDT, 0.45 MPa, 3.2 mm, unannealed | ° C. | 117 | 135 | ** |
| HDT, 1.82 MPa, 3.2 mm, unannealed | ° C. | 103 | 124 | ** |
| Optical |  |  |  |  |
| Light Transmission, 3.2 mm | % | 89 | 89 | ** |
| % Haze, 3.2 mm | % | <1 | <1 | ** |

** material too brittle-unable to mold proper test bars without cracking/shattering As can be seen from Table 2, Example 1 resulted in a polycarbonate composition with improved impact and thermal properties as compared to the polycarbonate of Comparative Examples 2 and 3, where Comparative Example 3 resulted in a material that was too brittle and was therefore unable to mold proper test bars without cracking or shattering. The improved melt flow rates at 300 and 250° C. of 100 and 19 g/10 min, respectively, of the polycarbonate composition used in Example 1 allows for the composition to pro-

TABLE 3

|  |  | Example 1 | Comparative Example 4 |
|---|---|---|---|
| Mechanical |  |  |  |
| Flexural modulus, 0.2 in/min | MPa | 2340 | 1170 |
| Tensile Stress, yield, Type 1, 0.2 in/min | MPa | 53 | 31.7 |

TABLE 3-continued

|  |  | Example 1 | Comparative Example 4 |
|---|---|---|---|
| Impact | | | |
| Izod impact, notched 23° C. | J/m | 596 | 32.0 |
| Izod impact, notched 23° C., % ductile | % | 100 | 0 |
| Physical | | | |
| Specific Gravity | — | 1.20 | 0.902 |
| Melt Flow Rate, 300° C., 1.2 kgf | cm³/10 min | 94 | — |
| Melt Flow Rate, 250° C., 1.2 kgf | cm³/10 min | 17.9 | — |
| Melt Flow Rate, 230° C., 1.2 kgf | cm³/10 min | 13.7 | 35 |
| Rockwell hardness (R-scale) | — | 120 | 89 |
| Thermal | | | |
| HDT, 0.45 MPa, 3.2 mm, unannealed | ° C. | 117 | 95 |

Table 3 shows that the polycarbonate of Example 1 has superior impact properties, stiffness values, as well as improved heat deformation values as compared to the polypropylene sample of Comparative Example 4.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and can or cannot be present in other embodiments. In addition, it is to be understood that the described elements can be combined in any suitable manner in the various embodiments.

The terms "bottom", and/or "top" are used herein, unless otherwise noted, merely for convenience of description, and are not limited to any one position or spatial orientation.

The endpoints of all ranges directed to the same component or property are inclusive and independently combinable (e.g., ranges of "less than or equal to 25 weight %, or 5 weight % to 20 weight %," is inclusive of the endpoints and all intermediate values of the ranges of "5 weight % to 25 weight %," etc.).

As used herein, the term "hydrocarbyl" and "hydrocarbon" refers broadly to a substituent comprising carbon and hydrogen, optionally with 1 to 3 heteroatoms, for example, oxygen, nitrogen, halogen, silicon, sulfur, or a combination thereof; "alkyl" refers to a straight or branched chain, saturated monovalent hydrocarbon group; "alkylene" refers to a straight or branched chain, saturated, divalent hydrocarbon group; "alkylidene" refers to a straight or branched chain, saturated divalent hydrocarbon group, with both valences on a single common carbon atom; "alkenyl" refers to a straight or branched chain monovalent hydrocarbon group having at least two carbons joined by a carbon-carbon double bond; "cycloalkyl" refers to a non-aromatic monovalent monocyclic or multicylic hydrocarbon group having at least three carbon atoms, "cycloalkenyl" refers to a non-aromatic cyclic divalent hydrocarbon group having at least three carbon atoms, with at least one degree of unsaturation; "aryl" refers to an aromatic monovalent group containing only carbon in the aromatic ring or rings; "arylene" refers to an aromatic divalent group containing only carbon in the aromatic ring or rings; "alkylaryl" refers to an aryl group that has been substituted with an alkyl group as defined above, with 4-methylphenyl being an exemplary alkylaryl group; "arylalkyl" refers to an alkyl group that has been substituted with an aryl group as defined above, with benzyl being an exemplary arylalkyl group; "acyl" refers to an alkyl group as defined above with the indicated number of carbon atoms attached through a carbonyl carbon bridge (—C(=O)—); "alkoxy" refers to an alkyl group as defined above with the indicated number of carbon atoms attached through an oxygen bridge (—O—); and "aryloxy" refers to an aryl group as defined above with the indicated number of carbon atoms attached through an oxygen bridge (—O—).

Unless otherwise indicated, each of the foregoing groups can be unsubstituted or substituted, provided that the substitution does not significantly adversely affect synthesis, stability, or use of the compound. The term "substituted" as used herein means that at least one hydrogen on the designated atom or group is replaced with another group, provided that the designated atom's normal valence is not exceeded. When the substituent is oxo (i.e., =O), then two hydrogens on the atom are replaced. Combinations of substituents and/or variables are permissible provided that the substitutions do not significantly adversely affect synthesis or use of the compound. Exemplary groups that can be present on a "substituted" position include, but are not limited to, cyano; hydroxyl; nitro; azido; alkanoyl (such as a $C_{2-6}$ alkanoyl group such as acyl); carboxamido; $C_{1-6}$ or $C_{1-3}$ alkyl, cycloalkyl, alkenyl, and alkynyl (including groups having at least one unsaturated linkages and from 2 to 8, or 2 to 6 carbon atoms); $C_{1-6}$ or $C_{1-3}$ alkoxy groups; $C_{6-10}$ aryloxy such as phenoxy; $C_{1-6}$ alkylthio; $C_{1-6}$ or $C_{1-3}$ alkylsulfinyl; $C_{1-6}$ or $C_{1-3}$ alkylsulfonyl; aminodi($C_{1-6}$ or $C_{1-3}$)alkyl; $C_{6-12}$ aryl having at least one aromatic rings (e.g., phenyl, biphenyl, naphthyl, or the like, each ring either substituted or unsubstituted aromatic); $C_{7-19}$ alkylenearyl having 1 to 3 separate or fused rings and from 6 to 18 ring carbon atoms, with benzyl being an exemplary arylalkyl group; or arylalkoxy having 1 to 3 separate or fused rings and from 6 to 18 ring carbon atoms, with benzyloxy being an exemplary arylalkoxy group.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While the disclosure has been described with reference to an exemplary embodiment, it will be understood by those skilled in the art that various changes can be made and equivalents can be substituted for elements thereof without departing from the scope of the disclosure. In addition, many modifications can be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The invention claimed is:

1. A microfluidic device, comprising
a fluid sample in a channel or microwell that includes a wall having a fabricated thickness of less than or equal to 1 mm formed from a thermoplastic composition comprising:

a poly(aliphatic ester)-polycarbonate comprising soft block ester units, derived from monomers comprising:
an alpha, omega $C_{6-20}$ aliphatic dicarboxylic acid or derivative thereof,
a dihydroxyaromatic compound, and
a carbonate source.

2. The microfluidic device of claim 1, wherein the alpha, omega $C_{6-20}$ aliphatic dicarboxylic acid or derivative thereof comprises sebacic acid.

3. The microfluidic device of claim 1, wherein the fabricated dimension is 0.005 to 1 mm.

4. The microfluidic device of claim 1, wherein the fabricated dimension is 0.01 to 0.5 mm.

5. The microfluidic device of claim 1, wherein the fabricated dimension is 0.05 to 0.2 mm.

6. The microfluidic device of claim 1, wherein the poly(aliphatic ester)-polycarbonate is of the formula (6b)

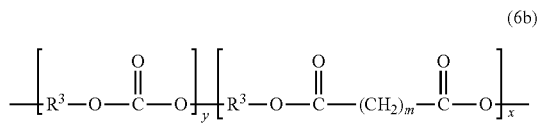

wherein m is 4 to 18, x and y each represent average weight percentages of the poly(aliphatic ester)-polycarbonate wherein the average weight percentage ratio x:y is 10:90 to 1:99, wherein x+y is 100, and each $R^3$ is independently derived from a dihydroxyaromatic compound of formula (3)

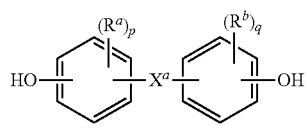

wherein $R^a$ and $R^b$ are each independently a halogen, $C_{1-12}$ alkoxy, or $C_{1-12}$ alkyl; $X^a$ is a single bond, —O—, —S—, —S(O)$_2$—, —S(O)$_2$—, —C(O)—, or a $C_{1-18}$ organic group; and p and q are each independently integers of 0 to 4 or formula (5)

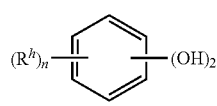

wherein each $R^h$ is independently a halogen atom, a $C_{1-10}$ hydrocarbyl such as a $C_{1-10}$ alkyl group, a halogen-substituted $C_{1-10}$ alkyl group, a $C_{6-10}$ aryl group, or a halogen-substituted $C_{6-10}$ aryl group, and n is 0 to 4.

7. The microfluidic device of claim 6, wherein the poly(aliphatic ester)-polycarbonate is of formula (6c)

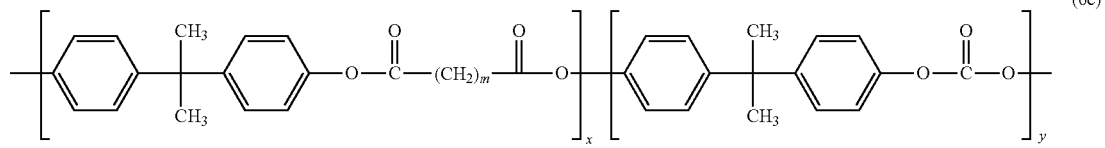
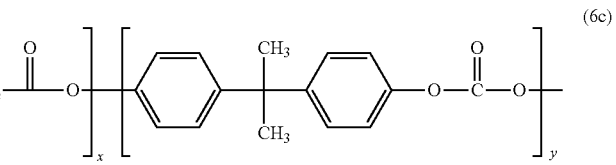

wherein m is 4 to 18 and wherein the average weight percentage ratio x:y is 10:90 to 1:99, wherein x+y is 100.

8. The microfluidic device of claim 6, wherein m is 8.

9. The microfluidic device of claim 1, wherein the thermoplastic composition has a melt flow rate of 66 to 150 g/10 min at 300° C. under a load of 1.2 kilograms according to ASTM D1238-10.

10. The microfluidic device of claim 1, wherein the thermoplastic composition has an HDT is 80 to 140° C. at 0.45 mega Pascal (MPa) with an unannealed 3.2 mm plaque according to ASTM D648-07.

11. The microfluidic device of claim 10, wherein the thermoplastic composition has a Notched Izod Impact (NII) ductility of 30 to 100%, with a ⅛-inch thick bar (3.18 mm) at 23° C. according to ASTM D256-10.

12. The microfluidic device of claim 1, wherein the thermoplastic composition has an HDT is 80 to 140° C. at 1.82 mega Pascal (MPa) with an unannealed 3.2 mm plaque according to ASTM D648-07.

13. The microfluidic device of claim 12, wherein the thermoplastic composition has a Notched Izod Impact (NII) ductility of 30 to 100%, with a ⅛-inch thick bar (3.18 mm) at 23° C. according to ASTM D256-10.

14. The microfluidic device method of claim 1, wherein the thermoplastic composition has a Notched Izod Impact (NII) ductility of 30 to 100%, with ⅛-inch thick bars (3.18 mm) at 23° C. according to ASTM D256-10.

15. The microfluidic device of claim 1, wherein the article has a Notched Izod Impact (NII) of 400 to 700 Joules per meter (J/m) with ⅛-inch thick bars (3.18 mm) at 23° C. according to ASTM D256-10.

16. The microfluidic device of claim 1, wherein the device is a PCR microwell device.

17. The microfluidic device of claim 16, wherein the PCR microwell device is a microwell sample container or a microwell cap.

18. The microfluidic device of claim 1, wherein the fluid is at a process temperature of at least 90° C.

19. The microfluidic device of claim 18, wherein the process temperature is less than or equal to 120° C.

20. The microfluidic device of claim 18, wherein the process temperature is less than or equal to 110° C.

21. The microfluidic device of claim 18, wherein the process temperature is at least 95° C.

22. The microfluidic device of claim 18, wherein the process temperature is from 95° C. to 105° C.

23. The microfluidic device of claim 18, wherein the process temperature is from 95° C. to 100° C.

24. The microfluidic device of claim 1, wherein the poly(aliphatic ester)-polycarbonate is derived from monomers consisting essentially of:

the alpha, omega $C_{6-20}$ aliphatic dicarboxylic acid or derivative thereof, the dihydroxyaromatic compound, and the carbonate source.

25. The microfluidic device of claim 1, wherein the channel or microwell is a PCR microwell.

26. A PCR microwell plate, comprising the PCR microwell of claim 25.

27. The microfluidic device of claim 1, wherein the wall having a fabricated thickness of less than or equal to 1 mm is a wall having a molded thickness of less than or equal to 1 mm.

28. The microfluidic device of claim 27, wherein the molded thickness is 0.005 to 1 mm.

29. The microfluidic device of claim 27, wherein the molded thickness is 0.01 to 0.5 mm.

30. The microfluidic device of claim 27, wherein the molded thickness is 0.05 to 0.2 mm.

* * * * *